(12) United States Patent
Yamane et al.

(10) Patent No.: US 6,207,378 B1
(45) Date of Patent: Mar. 27, 2001

(54) METHOD FOR AMPLIFYING NUCLEIC ACID MOLECULES AND METHOD FOR SYNTHESIZING PROTEINS

(75) Inventors: Tsuneo Yamane, Nagoya; Hideo Nakano, Iwakura; Masashi Ouchi; Reiko Okumura, both of Nagoya; Satoshi Sekiguchi, Tokyo, all of (JP)

(73) Assignee: Nippon Flour Mills Co., Ltd., Tokyo (JP)

( * ) Notice: Subject to any disclaimer, the term of this patent is extended or adjusted under 35 U.S.C. 154(b) by 0 days.

(21) Appl. No.: 09/136,411

(22) Filed: Aug. 19, 1998

(30) Foreign Application Priority Data

Aug. 19, 1997 (JP) ...................................... 9-222371
Oct. 16, 1997 (JP) .................................... 9-283904
Mar. 27, 1998 (JP) ................................. 10-081341

(51) Int. Cl.$^7$ ...................................... C12Q 1/68
(52) U.S. Cl. ............................................. 435/6; 435/91.2
(58) Field of Search ................................ 435/6; 439/91.2; 536/24.3

(56) References Cited

U.S. PATENT DOCUMENTS 4,683,195 * 7/1987 Mullis et al. ............................. 435/6

OTHER PUBLICATIONS

Gyllensten p. 300–306, in PCR Protocols, Ed. Innis et al., Academic Press, Inc., 1990.*

Innis et al., p. 3–12, in PCR Protocols, Ed. Innis et al., Academic Press, Inc., 1990.*

* cited by examiner

Primary Examiner—Scott W. Houtteman
(74) Attorney, Agent, or Firm—Oblon, Spivak, McClelland, Maier & Neustadt, P.C.

(57) ABSTRACT

A method for amplifying desired nucleic acid molecules by PCR which comprises the steps of isolating and purifying a group of nucleic acid molecules including desired nucleic acid molecules to be amplified, then carrying out PCR while establishing such a condition that the nucleic acid molecules capable of being amplified, except for primers, present in a PCR reaction solution are constituted by only the desired nucleic acid molecules and that the concentration of each primer used is limited to a level of not more than 100 nM; a method for producing a protein in a cell-free protein-synthesis system containing a cell-free extract which comprises using the nucleic acid of a single kind produced by the method described above and a method for establishing a protein library which comprises the steps of separately carrying out the method for amplifying desired nucleic acid molecules by PCR to obtain at least two kinds of nucleic acid molecules and separately carrying out the foregoing method for producing a protein using each of the at least two kinds of the amplified nucleic acids as a template to thus establish a protein library which comprises at least two kinds of proteins encoded by the resulting at least two nucleic acids respectively.

17 Claims, 2 Drawing Sheets

METHOD FOR AMPLIFYING NUCLEIC ACID MOLECULES AND METHOD FOR SYNTHESIZING PROTEINS

BACKGROUND OF THE INVENTION

The present invention relates to a method for amplifying nucleic acid molecules and in particular, to a method for amplifying nucleic acid molecules of a single kind. The present invention also pertains to a method for synthesizing a protein using a cell-free protein-synthesis system. Moreover, the present invention further relates to a method for constituting a protein library using the foregoing methods for amplifying nucleic acid molecules and for synthesizing proteins.

To preferentially amplify nucleic acid molecules of a single kind out of many kinds of nucleic acid molecules, there has been adopted a method which makes use of a combination of a plasmid and a host microorganism such as *Escherichia coli* or yeast. This method makes use of such a characteristic of the plasmid that only one plasmid molecule is taken in a host microorganism such as *E. coli* or yeast and comprises the steps of introducing a plasmid into a host microorganism by the calcium chloride method or the electroporation method, isolating-proliferating the microorganism to give a colony of the microorganism containing nucleic acid molecules of a single kind and to thus amplify the nucleic acid molecules of a single kind.

However, for instance, the linkage of a desired nucleic acid molecule to a plasmid, the introduction of the plasmid into a host microorganism and the isolation and proliferation of the microorganism require very complicated operations and as a result, they require the use of an advanced technology and a great deal of expenses and time. In particular, DNA molecules of a single kind should be isolated from vast kinds of DNA molecules in the field wherein industrially useful proteins are produced by altering the base sequences of genetic DNA's coding for amino acid sequences, producing variant proteins whose amino acid sequences are changed by using the resulting DNA variants, but it is very difficult to practice such operations.

Moreover, in the cell-free protein-synthesis system, the operations required for the synthesis of proteins are quite simple as compared with the protein-synthesis system which makes use of, for instance, organisms or living cells such as cultured cells and for this reason, there has recently been desired for the development of such a cell-free system. In addition, the PCR (polymerase chain reaction) technique is an extremely effective and simple means for amplifying DNA genes. Under such circumstances, there has been desired for the development of a technique, which comprises the combination of these two techniques, for easily and directly synthesizing a large amount of proteins using the DNA's which code for the proteins and which are produced by the PCR technique without using any plasmid DNA.

There has already been known a cell-free protein-synthesis system using DNA's produced by the PCR technique (Proc. Natl. Acad. Sci. USA, 1997, 94, pp. 412–417). However, it has been difficult to synthesize a protein in a desired amount and therefore, it has been an important subject to improve the yield of proteins synthesized by this technique.

SUMMARY OF THE INVENTION

Accordingly, it is a first object of the present invention to provide a method for easily and effectively amplifying nucleic acid molecules of a single kind.

It is a second object of the present invention to provide a method for easily producing a protein in a sufficient amount, which makes use of a cell-free protein-synthesis system.

It is a third object of the present invention to provide a method for efficiently and easily constituting a protein library.

The inventors of this invention have conducted various studies to accomplish the foregoing objects, have found that only desired nucleic acid molecules of a single kind can efficiently be amplified by isolating and purifying a group of nucleic acid molecules including the desired nucleic acid molecules to be amplified and carrying out PCR (polymerase chain reaction) procedures at a very low molar concentration of the desired nucleic acid molecules using primers each at a sufficiently low concentration and have thus completed the present invention.

Thus, according to a first aspect of the present invention, there is provided a method for amplifying desired nucleic acid molecules by PCR which comprises the steps of isolating and purifying a group of nucleic acid molecules including the desired nucleic acid molecules to be amplified, then carrying out PCR procedures while establishing such a condition that the nucleic acid molecules capable of being amplified, except for primers, present in a PCR reaction solution are constituted by only the desired nucleic acid molecules and that the concentration of each primer used is limited to a level of not more than 100 nM. In this regard, the term "nucleic acid molecules of a single kind" is herein used to mean DNA, RNA or both represented by base sequence.

According to a second aspect of the present invention, there is provided a method for producing a protein in a cell-free protein-synthesis system containing a cell-free extract, which is characterized by using the nucleic acid of a single kind produced by the foregoing method of the present invention as a template. The term "cell-free protein-synthesis system" used herein means both cell-free translation systems which read the information of mRNA's and synthesize proteins or polypeptides and systems each comprising a cell-free transcription system wherein an RNA is synthesized using a DNA as a template and a cell-free translation system.

According to a further aspect of the present invention, there is provided a method for establishing a protein library which comprises the steps of separately carrying out the foregoing nucleic acid-amplification method of the present invention to obtain at least two kinds of nucleic acid molecules and separately carrying out the foregoing protein-production method of the present invention using each of the at least two kinds of the amplified nucleic acids as a template to thus establish a protein library which comprises at least two kinds of proteins encoded by the resulting at least two amplified nucleic acids respectively.

DESCRIPTION OF THE PREFERRED EMBODIMENTS

Figure 1:
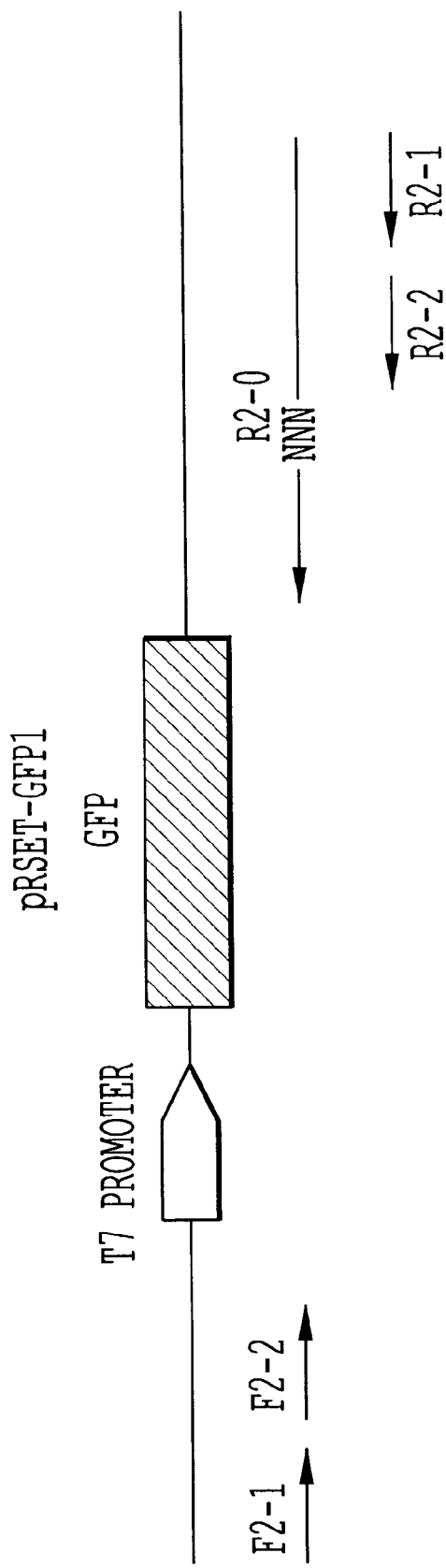
FIG. 1 is a diagram showing the DNA fragment used as a template in Example 1 and obtained by digesting the plasmid pRSET-GFP1 with ScaI as well as the position of each primer.

The nucleic acid molecules to be amplified by the method of the present invention include DNA and RNA molecules.

The step for isolating and purifying a group of nucleic acid molecules and the step of the PCR reaction in the method of the invention will be detailed below.

i. Isolation and Purification of a Group of Nucleic Acid Molecules Containing Desired Nucleic Acid Molecules The group of nucleic acid molecules containing the desired nucleic acid molecules usable in the present invention may be any group of nucleic acid molecules which can serve as substrates in PCR reactions, such as DNA's linked by ligation reactions and DNA's synthesized through reverse transcription reactions from RNA's.

The isolation and purification of the group of nucleic acid molecules may vary depending on source materials used, but may be practiced according to any method commonly used such as the HPLC (high-performance liquid chromatography) method, the electrophoretic method, the biotinylated primer-avidin method and the primer-immobilized tube method. However, it is necessary to select a method which never damages the desired nucleic acid molecules and can effectively isolate and purify the nucleic acid molecules.

The elimination of this step of isolating-purifying the group of the desired nucleic acid molecules would often lead to the amplification of nucleic acid molecules completely different from the desired ones. In the present invention, therefore, nucleic acid molecules possibly present in a sample other than the desired nucleic acid molecules should be removed by carrying out the isolation and purification of the latter. Examples of the nucleic acid molecules other than the desired molecules are contaminated DNA's derived from, for instance, experimental tools and hands and primers used when a sample is prepared by amplifying the desired nucleic acid molecules by the PCR technique.

In the present invention, the isolation and purification of the group of nucleic acid molecules including the desired nucleic acid molecules to be amplified can provide a group of nucleic acid molecules consisting essentially of nucleic acids having molecular weights almost identical to each other.

ii. Method for Obtaining Only Desired Nucleic Acid Molecules

In the present invention, a variety of methods can be used as means for establishing such a condition that the nucleic acid molecules capable of being amplified present in the PCR reaction solution other than the primers simply consist of the desired nucleic acid molecules, but the simplest method is to dilute the solution obtained after the isolation and purification of the group of nucleic acid molecules including the desired molecules. The dilution operation easily permits the establishment of the condition that the PCR reaction solution simply consists of one or at least two nucleic acid molecules of a single kind capable of being amplified other than the primers, i.e., the condition that the nucleic acid molecules capable of being amplified other than the primers consist only of the desired nucleic acid molecules. Upon dilution, it is desirable to add, for instance, tRNA molecules in order to prevent any adsorption of nucleic acid molecules on the wall of a tube. The amount thereof to be added suitably ranges from about 0.1 to 10 µg/ml.

iii. Concentration of Primers in PCR Reaction Solution

In the present invention, the PCR reaction should be carried out at a concentration of each primer, in the PCR reaction solution, of not more than 100 nM, preferably not more than 10 nM. This is because if the primer concentration exceeds 100 nM, a non-specific amplification reaction is apt to cause between primers and this results in the occurrence of amplification between primers such as the formation of so-called dimerized primers, the reduction of amplification efficiency of the desired nucleic acid molecules and the reduction of the yield thereof.

iv. Thermostable Polymerase

This enzyme may be any commonly used polymerase. In addition, the PCR reaction is desirably initiated according to the hot-start method to prevent the formation of dimerized primers.

In the present invention, the amplification of only the nucleic acid molecules of a single kind can be confirmed by determining the sequence of, for instance, the DNA per se or the product obtained by cloning the DNA into a plasmid.

In the first aspect of the present invention, the foregoing PCR is preferably the nested-PCR technique.

Next, the method for producing a protein in a cell-free protein-synthesis system including a cell-free extract will hereunder be described in detail.

In the present invention, the nucleic acids used as templates are not restricted to any particular one inasmuch as they are obtained by the foregoing amplification method of the present invention. However, preferred are template DNA's which comprise a promoter DNA sequence, a ribosome binding DNA sequence, a DNA sequence coding for a desired protein and a terminator DNA sequence or a variant terminator DNA sequence and in which the sum of the foregoing 4 kinds of DNA sequences is not less than 50% of the total DNA sequence.

The promoter sequence is a DNA sequence to which an RNA polymerase is first linked when synthesizing an mRNA; the ribosome binding DNA sequence is a DNA sequence of the site, to which a ribosome (a complex controlling the protein synthesis) is linked upon synthesis of a protein after the DNA is converted to the mRNA; and the terminator DNA sequence or the variant terminator DNA sequence is a sequence (transcription-termination sequence) for terminating the synthesis of mRNA's by an RNA polymerase. In the present invention, it is preferred to use a template DNA obtained by linking the foregoing 4 kinds of DNA sequences in this order and in which the sum of these DNA sequences is not less than 50% of the total DNA sequence. This is because, if the sum of the foregoing 4 kinds of DNA sequences is less than 50% of the total DNA sequence, it is necessary to synthesize a DNA sequence which is not directly involved in the synthesis of a protein in addition to the DNA fragments required for the protein synthesis and to then link it to the latter and this leads to an increase in the DNA-production cost and a decrease in the protein-synthesis efficiency.

As the cell-free extract used in the present invention, there may be listed, for instance, a wheat germ extract, an *E. coli* cell extract and a rabbit reticulocyte extract.

We will hereunder describe, in detail, every step from the preparation of the cell-free extract used in the present invention to the determination of the protein activity of the cell-free protein-synthesis system.

i. Preparation of Cell-Free Extract

The method for preparing a cell-free extract may be selected depending on the source materials used, but the extract may be prepared by any method commonly used.

ii. Cell-Free Protein-Synthesis Reaction

The reaction solution may comprise, in addition to the cell-free extract, the DNA coding for the desired protein, tRNA, an RNA polymerase, the protein-constituting amino acids, a buffering agent, an energy source such as ATP and GTP, an ATP regenerating system such as creatine phosphate, creatine phosphokinase, phosphoenolpyruvic acid and pyruvate kinase, a stabilizer such as dithiothreitol (DTT), spermine and spermidine, and an RNase inhibitor in appropriate amounts. The reaction is carried out at an optimum temperature which varies depending on the cell-free extract used and the kind of the desired protein and which in general suitably ranges from 20 to 40° C.

The information concerning an amino acid sequence used for synthesizing a protein is given to the protein-synthesis system in the form of an mRNA. This mRNA is synthesized through a transcription reaction by an RNA polymerase based on the template DNA. The RNA polymerase first recognizes a promoter sequence specific to the kind of the polymerase, links to the portion and then initiates the synthesis of the corresponding RNA. The RNA synthesis is spontaneously completed at an instance when the DNA sequence is exhausted (run-off method) or at an instance when the terminator sequence specific to the kind of the RNA polymerase used appears. In the method which has widely been used and in which a plasmid DNA is used as a template, there has not been observed any difference in the efficiency of protein-synthesis between the run-off method and the method using a terminator sequence. For this reason, the simpler run-off method has widely been used.

However, when the DNA's as PCR products are used as templates, there is observed such a tendency that the efficiency of protein-synthesis achieved by the run-off method is inferior to that achieved by the method using a plasmid. Accordingly, we have investigated for the causes thereof and have further advanced the studies to improve the efficiency of protein-synthesis. As a result, it has been confirmed that the efficiency of protein-synthesis can significantly be improved when a protein is prepared using a template DNA in which a terminator sequence or a variant terminator sequence is linked to the template DNA coding for the desired protein (at 3'-terminal side) and in which the sum of the promoter sequence, the ribosome binding DNA sequence, the DNA sequence coding for the desired protein, and the terminator sequence or the variant terminator sequence is not less than 50% of the total DNA sequence.

The reason why the amount of the protein synthesized (protein-synthesis activity) is increased by the method of the present invention has not yet been clearly elucidated, but it would be assumed that the protein-synthesis activity is improved, for instance, due to the facts that the mRNA produced by the RNA polymerase is stabilized, that the amount of the mRNA synthesized is increased and that the higher-order structure of the mRNA effectively functions in the protein-synthesis system.

The RNA polymerase used in the present invention may be those commonly used and having any sequence. However, desirably used are RNA polymerases derived from viruses such as T7, T3 and SP6 while taking into consideration the activity thereof in the protein-synthesis reaction solution and easy availability of the RNA polymerase per se.

Moreover, the terminator DNA sequence or the variant terminator DNA sequence used in the invention may be any DNA sequence inasmuch as they have abilities of terminating the transcription reaction of the RNA polymerase and of liberating the synthesized RNA from the corresponding DNA. It is usually desirable to use the terminator DNA sequence specific to the RNA polymerase used in the transcription reaction. However, it is clear that any DNA sequence which corresponds to the terminator DNA sequence specific to the RNA polymerase in which a part of the bases are subjected to substitution, deletion or insertion may likewise be used in the invention so far as they can serve to terminate the transcription reaction of the RNA polymerase or to liberate the synthesized RNA from the corresponding DNA and the terminator DNA sequences of this kind are referred to as "variant terminator DNA sequence" in this specification.

The present invention further provides a method for establishing a protein library which comprises the steps of separately carrying out the foregoing nucleic acid-amplification method of the present invention to obtain at least two kinds of nucleic acid molecules and separately carrying out the foregoing protein-production method of the present invention using each of said at least two kinds of the amplified nucleic acids as a template to thus establish a protein library which comprises at least two kinds of proteins encoded by the resulting at least two amplified nucleic acids respectively. Thus, a protein library comprising desired proteins can efficiently and easily be established by carrying out the amplification method and the protein-production method of the present invention using several kinds of desired nucleic acid molecules.

The present invention will hereinafter be described in more detail with reference to the following Examples and Comparative Examples, but the present invention is not restricted to these specific Examples at all.

EXAMPLE 1

Amplification of Nucleic Acid

Preparation of A Group of Nucleic Acid Molecules to be Amplified

A PCR reaction procedures were conducted under the following conditions, using the DNA fragments obtained by digesting the plasmid pRSET-GFP1 shown in FIG. 1 with ScaI as templates.

The primer R2-0 used herein includes N's (mixture of A, G, C, T) at three positions and a mixture of $4^3$ kinds of molecules, i.e., 64 kinds of DNA molecules.

TABLE 1

|  | Final Concn. in Reaction Soln. |
| --- | --- |
| Template DNA | 2 ng/ml |
| Primer F2-1 | 1000 nM |
| Primer R2-0 | 1000 nM |
| dNTPs | 0.2 mM each |
| Taq DNA Polymerase (TaKaRa) | 40 U/ml |
| Total Amount | 50 µl | dNTPs: deoxynucleotide triphosphates (a mixture of 4 kinds of bases)

The reaction solution was pre-heated at 94° C. for 3 minutes, followed by executing 30 cycles of the following cycle program: 96° C.×15 sec, 55° C.×30 sec and 72° C.×60 sec, and subsequent further extension at 72° C. for additional 10 minutes.

Then the reaction solution was subjected to a phenol/chloroform treatment and an ethanol-precipitation treatment and the resulting solution was further purified by HPLC under the following conditions:

Column: TOSOH TSKgel DEAE-NPR

Temp.: 25° C.

Eluent: A. 20 mM Tris-HCl (pH 9.0) B. 20 mM Tris-HCl (pH 9.0)+1.0M NaCl

The elution was carried out according to the following program: 0 min. (B: 0%), 10 min. (B: 50%), 30 min. (B: 70%) and 50 min. (B: 100%).

In the HPLC purification, the flow rate was set at 0.5 ml/min and the detection was carried out by determining absorbance at 260 nm.

The fractions recovered were subjected to a phenol/chloroform treatment and an ethanol-precipitation treatment and then the resulting precipitates were dissolved in TE buffer.

The solution was further subjected to PCR reaction under the following conditions in order to eliminate double-stranded DNA's other than a group of nucleic acid molecules containing the desired nucleic acid molecules:

TABLE 2

|  | Final Concn. in Reaction Soln. |
| --- | --- |
| Template DNA | 5 µg/ml |
| Primer F2-1 | 1000 nM |
| Primer R2-1 | 1000 nM |
| dNTPs | 0.2 mM each |
| Taq DNA Polymerase (TaKaRa) | 40 U/ml |
| Total Amount | 50 µl |

The reaction solution was pre-heated at 94° C. for 3 minutes, followed by executing 5 cycles of the following cycle program: 96° C.×15 sec, 53° C.×30 sec and 72° C.×60 sec. and subsequent further extension at 72° C. for additional 10 minutes.

The reaction product thus obtained was purified by HPLC as described above to give a group of nucleic acid molecules to be amplified.

Dilution of Group of Nucleic Acid Molecules Containing Desired Nucleic Acid Molecules The foregoing DNA's purified by HPLC were diluted. In this respect, a solution of $10^{12}$ molecules/ml was diluted in order with a 1.0 µg/ml tRNA (Sigma) solution to give a diluted solution having a concentration of $10^3$ molecules/ml, in order to prevent any loss of DNA molecules due to the adsorption thereof on, for instance, the wall of a tube used. A sample (1 µl) was taken from the resulting diluted solution and used in the following PCR procedures.

Amplification of Single Kind of Molecules

The PCR procedures were performed under the following conditions, using the nucleic acid molecules present in the diluted solution as templates.

TABLE 3

|  | Final Concn. in Reaction Soln. |
| --- | --- |
| Template DNA | A sufficiently diluted solution, which is considered to be one containing a single kind of DNA molecules |
| Primer F2-1 | 100 nM |
| Primer R2-1 | 100 nM |
| dNTPs | 0.2 mM each |
| Taq DNA Polymerase (TaKaRa) | 40 U/ml |
| Total Amount | 10 µl |

The reaction solution was pre-heated at 94° C. for 3 minutes, followed by executing 50 cycles of the following cycle program: 96° C.×15 sec, 53° C.×30 sec and 72° C.×60 sec, and subsequent further extension at 72° C. for additional 10 minutes.

The PCR procedures were further carried out under the following conditions, using the nucleic acid molecules present in the reaction solution as templates.

TABLE 4

|  | Final Concn. in Reaction Soln. |
| --- | --- |
| The Foregoing FCR Reaction Solution | 1 µl |
| Primer F2-2 | 500 nM |
| Primer R2-2 | 500 nM |
| dNTPs | 0.2 mM each |
| Taq DNA Polymerase (TaKaRa) | 40 U/ml |
| Total Amount | 11 µl |

The reaction solution was pre-heated at 94° C. for 3 minutes, followed by executing 30 cycles of the following cycle program: 96° C.×15 sec, 58° C.×30 sec and 72° C.×60 sec, and subsequent further extension at 72° C. for additional 10 minutes.

The reaction products were analyzed by the agarose gel electrophoresis and it was thus confirmed that a DNA band having a desired length was formed.

COMPARATIVE EXAMPLE 1

The same procedures used in Example 1 were repeated except that the purification by HPLC was omitted and that the concentrations of the Primers F2-1 and R2-1 were changed to 1 µM, respectively, when practicing PCR procedures in the step for amplification of DNA molecules of a single kind.

The base sequences of the primers used are listed in the following Table 5.

TABLE 5

| Primer for PCR | Sequence |  |
| --- | --- | --- |
| F2 - 1 | 5' GCGAGTCAGT GAGCGAGGAA G 3' | (SEQ ID NO:1) |
| F2 - 2 | 5' CGATTCATTA ATGCAGATCT CGAATCCC 3' | (SEQ ID NO:2) |
| R2 - 0 | 5' AACAGTACAC GTCGTGCCAC CAAAGCAGAG AGCTCCACTG TCTCGCCAAN NNGATCAAGC TTCGAATTCT ACGAATGCTA 3' | (SEQ ID NO:3) |
| R2 - 1 | 5' AACAGTACAC GTCGTGCCAC C 3' | (SEQ ID NO:4) |
| R2 - 2 | 5' AGCAGAGAGC TCCACTGTCT CGCC 3' | (SEQ ID NO:5) |

The sequence of the NNN portion of the clones obtained in Example 1 and its cloning number are summarized in the following Table 6.

TABLE 6

Sequence of NNN Portion and Its Cloning Number

| 1st Base | A | | | | C | | | | G | | | | T | | | |
|---|---|---|---|---|---|---|---|---|---|---|---|---|---|---|---|---|
| 2nd Base | A | C | G | T | A | C | G | T | A | C | G | T | A | C | G | T |
| 3rd Base A | 0 | 1 | 0 | 1 | 1 | 0 | 0 | 1 | 0 | 0 | 0 | 0 | 1 | 1 | 0 | 0 |
| C | 2 | 0 | 2 | 0 | 1 | 1 | 0 | 0 | 0 | 0 | 1 | 0 | 0 | 1 | 0 | 0 |
| G | 0 | 1 | 1 | 1 | 0 | 0 | 1 | 0 | 0 | 0 | 1 | 0 | 1 | 0 | 0 | 1 |
| T | 1 | 0 | 0 | 0 | 1 | 1 | 0 | 0 | 1 | 0 | 0 | 0 | 0 | 1 | 0 | 0 |

Each of the DNA's obtained from the final PCR reaction solution had a single sequence and thus 24 kinds of clones out of the expected 64 kinds of sequences were obtained.

Contrary to this, the DNA's obtained from the final PCR reaction solution of Comparative Example 1 were likewise analyzed by agarose gel electrophoresis, but there was not detected any DNA band having a desired length.

As has been discussed above, in the present invention, a group of nucleic acid molecules including the desired nucleic acid molecules to be amplified are isolated and purified, then PCR procedures are carried out while establishing such a condition that the nucleic acid molecules capable of being amplified, except for primers, present in the PCR reaction solution are constituted by only the desired nucleic acid molecules and that the concentration of each primer used is limited to a level of not more than 100 nM. Accordingly, the method of the present invention permits the amplification of nucleic acid molecules of a single kind easily and efficiently.

EXAMPLE 2

Synthesis of Protein

Preparation of *E. coli* Extract

An *E. coli* extract was prepared according to the method of Ellman et al. (Methods Enzymol., 1991, 202: 301–336).

More specifically, *E. coli* A19 was first cultured at 37° C. in a jar fermentor containing 8 l of a culture medium and the proliferation thereof was stopped at an instance when the absorbance at 450 nm reached 1.1. The bacterial cells were collected by centrifugation, suspended in a buffer and then disrupted at 8400 psi in a French press. Immediately thereafter, the suspension containing the disrupted bacterial cells was centrifuged at 30,000×g to give a supernatant (S30). To the resulting supernatant, there was added a buffer supplemented with an energy source such as ATP and the mixture was then slowly shaken at 37° C. for 80 minutes. Subsequently, the liquid was dialyzed 3 times at 4° C. for 45 minutes and further centrifuged at 4,000×g to give a supernatant which was used as the *E. coli* extract.

Cell-Free Protein-Synthesis Reaction

The cell-free protein-synthesis was performed according to the method developed by Toshiya ENDO et al. (69th Meeting of the Biochemical Society of Japan, 4-P-1209).

The reaction solution of Example 2 comprises 56.4 mM Tris.HCl buffer (pH 7.4), 1.22 mM ATP, 0.85 mM each of GTP, UTP and CTP, 1.76 mM DTT, 40 mM creatine phosphate, 0.15 mg/ml creatine kinase, 320 $\mu$M amino acid, 10 mM magnesium acetate, 150 mM potassium acetate, 4% PEG, 34.6 $\mu$g/ml folinic acid, 35.9 mM NH$_4$OAc, 10 $\mu$g/ml rifampicin, 0.17 mg/ml *E. coli* tRNA, 0.02 mg/ml of the template DNA, 10 $\mu$g/ml of the T7 RNA polymerase, and 0.2 ml of the *E. coli* extract and the total volume thereof was adjusted to 1 ml. The reaction was carried out at 37° C. for 2 hours.

Figure 2:
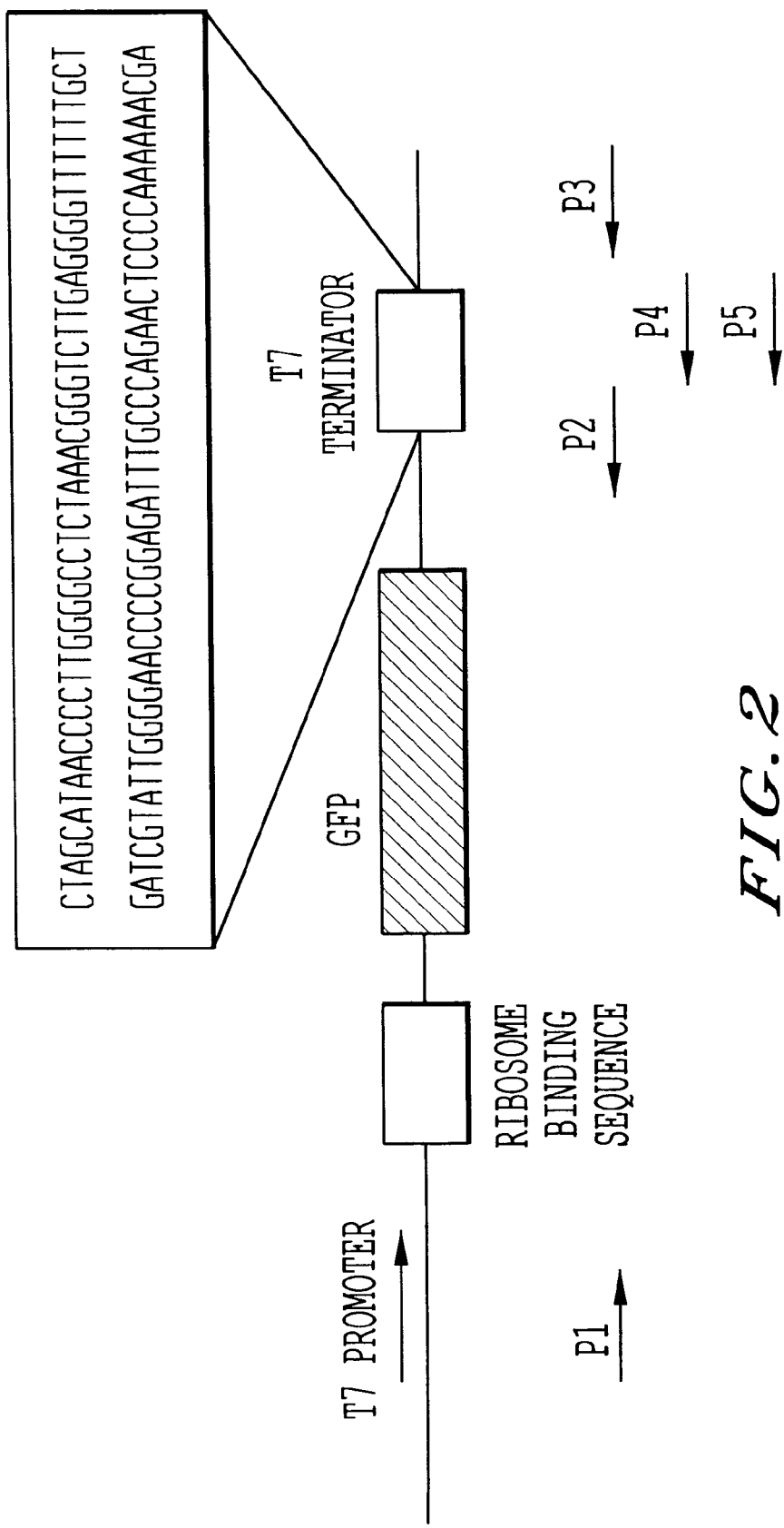
FIG. 2 is a diagram showing the DNA sequence used as a template in Example 2, among the DNA sequences of the plasmid pRSET-GFP1.

In this regard, the template DNA used in Example 2 was obtained by executing PCR procedures using the plasmid pRSET-GFP1 including a T7 promoter sequence, a GFP (green fluorescein protein: fluorescent protein originated from a jellyfish) gene sequence and T7 terminator sequence as a template and using a sense primer P1 including a T7 promoter sequence and an antisense primer P3 carrying a sequence downstream a T7 terminator sequence. On the other hand, the plasmid pRSET-GFP1 was established by treating the plasmid pGFP (Clonetech Company) with restriction enzymes BamHI and EcoRI to cut the GFP gene out of the plasmid and then the gene was inserted between the BamHI and EcoRI sites of the plasmid pRSETB (Invitrogen Company). Among the DNA sequence of the plasmid pRSET-GFP1, the fragment used in this Example as a template has the DNA constitution as shown in FIG. 2. The T7 promoter sequence and the ribosome binding DNA sequence used herein are as follows:

```
T7 Promoter Sequence:        TAATACGACTCACTATA
                             ATTATGCTGAGTGATAT Ribosome-Linked DNA Sequence:    AAGGAG
                                 TTCCTC
                                 (SEQ ID NO:13)
```

EXAMPLE 3

Synthesis of Protein

The reaction of this Example was carried out using a reaction solution having the same composition used in Example 2. In addition, the template DNA used herein was a short template DNA produced by executing PCR procedures using the same plasmid used in Example 2 as a template and using a sense primer P1 including the T7 promoter sequence and an antisense primer P2 immediately upstream the T7 terminator sequence.

After one hour from the initiation of the reaction, a part of the reaction solution was taken to determine the amount of GFP synthesized by measuring the fluorescence (excitation wavelength of 395 nm and emission wavelength of 509 nm). In this respect, the amount of the protein synthesized is expressed in terms of the value obtained by subtracting the background fluorescence observed at the reaction time of 0 from the intensity of the fluorescence emitted by the GFP protein synthesized after the lapse of a predetermined time.

EXAMPLES 4 AND 5

Synthesis of Proteins

To prove the effectiveness of the terminator sequence shown in Example 2, the lengths of the template DNA's are made uniform and there were used a template DNA carrying the T7 terminator sequence in Example 4 and a template DNA whose T7 terminator sequence was partially (6 bases) changed in Example 5.

Preparation of *E. coli* Extract and Cell-Free Protein-Synthesis Reaction

The preparation of an *E. coli* extract and a cell-free protein-synthesis reaction were carried out by the same methods used in Example 2, provided that the template DNA used in Example 4 was prepared by executing PCR procedures using the same plasmid used in Example 2 as a template and using a sense primer P1 including the T7 promoter sequence and an antisense primer P4 including the T7 terminator sequence, while that used in Example 5 was prepared by executing PCR procedures using a sense primer P1 including the T7 promoter sequence and an antisense primer P5 including the T7 terminator sequence which was partially (6 bases) altered.

The base sequences of the primers used in the PCR procedures are listed in the following Table 7.

TABLE 7

| Primer | Base Sequence | |
|---|---|---|
| P1 | CCGCGAAATT AATACGACTC | (SEQ ID NO: 6) |
| P 2 | TTATTGCTCA GCGGTGGCAG | (SEQ ID NO: 7) |
| P 3 | GCCAGATCCG GATATAGTTC CTCC | (SEQ ID NO: 8) |
| P 4 | AGCAAAAAAC CCCTCAAGAC C | (SEQ ID NO: 9) |
| P 5 | AGCAAAAATC GTCTCAACAA GCGTTTAGAG GCCCCAAGGG GT | (SEQ ID NO:10) |

The results obtained are summarized in the following Table 8.

TABLE 8

| Example No. | Amt. of GFP Synthesized (relative Amt.) |
|---|---|
| 2 (T7 terminator of its complete length was linked) | 15 |
| 3 (free of any linked terminator) | 2.2 |
| 4 (T7 terminator of its complete length was linked) | 13 |
| 5 (T7 terminator of its complete length was partially altered) | 4.3 |

The results listed in Table 8 clearly indicate that the amount of the protein (GFP) synthesized in Example 2 using the template DNA to which the T7 terminator DNA sequence having its complete length is linked is 6.8 times that synthesized in Example 3 using the template DNA free of any linked T7 terminator DNA sequence.

The results listed in Table 8 also indicate that the amount of the protein (GFP) synthesized in Example 4 using the template DNA to which the T7 terminator DNA sequence having its complete length is linked is 5.9 times that synthesized in Example 3 using the template DNA free of any linked T7 terminator DNA sequence.

Furthermore, the results listed in Table 8 indicate that the amount of the protein synthesized in Example 5 using the template DNA to which the terminator DNA sequence having a length equal to that of the terminator DNA sequence used in Example 4 and partially altered (variant terminator DNA sequence) is linked is smaller than that observed in Example 4, but is two times the amount of the protein synthesized in Example 3 using the template DNA free of any linked T7 terminator DNA sequence.

The foregoing results indicate that the use of a template DNA to which a terminator DNA sequence having its complete length permits a considerable increase in the amount of a protein synthesized and that the use of a variant terminator DNA sequence obtained by partially altering a terminator DNA sequence leads to a decrease in the effect expected by linking a terminator DNA sequence.

EXAMPLES 6 AND 7

Synthesis of Proteins

In these Examples, PCR procedures were performed under conditions similar to those used in Example 1 while using, as a template, a DNA fragment obtained by digesting the plasmid pRSET-GFP1 shown in FIG. 1 with ScaI. Among the DNA's finally obtained using primers F2-2 and R2-2, the DNA whose NNN portion was AAC was used in the following experiments.

Production of T7 Terminator Sequence

PCR procedures were performed under conditions similar to those used in Example 1 while using, as a template, a DNA fragment obtained by digesting the plasmid pRSET-GFP1 with ScaI to thus give a T7 terminator sequence capable of being linked to the foregoing sequence.

TABLE 9

| | Final Concn. in Reaction Soln. |
|---|---|
| Template DNA | 1 ng/50 µl |
| Primer F-T7TER-1 | 1000 nM |
| Primer pRSET-13-32 | 1000 nM |
| dNTPs | 0.2 mM each |
| Taq DNA Polymerase (TaKaRa) | 40 U/ml |
| Total Amount | 50 µl |

The reaction solution was pre-heated at 94° C. for 3 minutes, followed by executing 30 cycles of the following cycle program: 96° C.×15 sec, 55° C.×30 sec and 72° C.×30 sec, and subsequent further extension at 72° C. for additional 10 minutes.

The resulting DNA fragment was purified by HPLC under the same conditions used in Example 1 to give a T7 terminator fragment. Then this T7 terminator fragment was added to the foregoing DNA fragment obtained by one molecular PCR.

TABLE 10

| | Final Concn. in Reaction Soln. |
|---|---|
| DNA obtained by One Molecular PCR (the sequence of the NNN portion is AAC) | 1 ng/50 μl |
| T7 Terminator Fragment | 1 ng/50 μl |
| Primer F2-2 | 500 nM |
| Primer PRSET-13-32 | 500 nM |
| dNTPs | 0.2 mM each |
| Taq DNA Polymerase (TaKaRa) | 40 U/ml |
| Taq Start Antibody (Clonetech) | 1.76 ng/ml |
| Total Amount | 10 μl |

The reaction solution was pre-heated at 94° C. for 3 minutes, followed by executing 30 cycles of the following cycle program: 96° C.×15 sec, 58° C.×30 sec and 72° C.×60 sec, and subsequent further extension at 72° C. for additional 10 minutes.

The base sequences of the primers used in the PCR reaction are shown in the following Table 11.

TABLE 11

| Primer | Base Sequence |
|---|---|
| F-T7TER-1 | GGCGAGACAG TGGAGCTCTC TGCCCGGCTG CTAACAAAGC C |
| pRSET-13-32 | CTGCGCAACT GTTGGGAAGG G |

Then the preparation of an *E. coli* extract and the cell-free protein-synthesis reaction were performed by the same methods used in Example 2. The results thus obtained are summarized in the following Table 12.

TABLE 12

| Example No. | Amt. of GFP Synthesized (relative Amt.) |
|---|---|
| 6 (T7 terminator of complete length was linked) | 3.6 |
| 7 (free of any linked terminator) | 0.79 |

The foregoing results of Table 12 clearly indicate that the use of a template DNA to which a terminator DNA sequence of its complete length is linked permits a significant increase in the amount of proteins synthesized.

What is claimed is:

1. A method of amplifying a target nucleic acid comprising:
   isolating the target nucleic acid from a nucleic acid sample, wherein the target nucleic acid consists of a nucleic acid molecule to be amplified;
   amplifying the isolated target nucleic acid with amplification primers, wherein the concentration of the primers is not more than 100 nm.

2. The method of claim 1, wherein the isolating comprises diluting the nucleic acid sample and removing a portion of the dilution, wherein said portion does not contain nucleic acids other than the target nucleic acid.

3. The method of claim 1, wherein the isolating comprises subjecting the nucleic acid sample to HPLC and recovering the target nucleic acid.

4. The method of claim 1, wherein the concentration of the primers is not more than 10 nm.

5. The method of claim 1, wherein said target nucleic acid comprises a promoter DNA sequence, a ribosome binding sequence, a protein coding sequence, and a terminator or variant terminator DNA sequence.

6. The method of claim 5, wherein said target nucleic acid comprises not less than 50% of the promoter DNA sequence, the ribosome binding sequence, the protein coding sequence and the terminator or variant terminator DNA sequence.

7. A method of producing a protein comprising reacting the amplified target nucleic acid of claim 1 in a cell-free protein-synthesizing system.

8. The method of claim 7, wherein the cell-free protein synthesizing system comprises T7 RNA polymerase.

9. The method of claim 7, wherein the cell-free protein synthesizing system comprises an *E. Coli* extract.

10. A method of making a protein library comprising:

(A) isolating the target nucleic acid from a nucleic acid sample, wherein the target nucleic acid consists of a nucleic acid molecule to be amplified;

(B) amplifying the isolated target nucleic acid with amplification primers, wherein the concentration of the primers is not more than 100 mm;

(C) reacting the amplified target nucleic acid in a cell-free protein-synthesizing system;

(D) repeating steps (A), (B), and (C) at least one time for another target nucleic acid.

11. The method of claim 10, wherein the isolating comprises diluting the nucleic acid sample and removing a portion of the dilution, wherein said portion does not contain nucleic acids other than the target nucleic acid.

12. The method of claim 10, wherein the isolating comprises subjecting the nucleic acid sample to HPLC to recover the target nucleic acid.

13. The method of claim 10, wherein the concentration of the primers is not more than 10 mm.

14. The method of claim 10, wherein said target nucleic acid comprises a promoter DNA sequence, a ribosome binding sequence, a protein coding sequence, and a terminator or variant terminator DNA sequence.

15. The method of claim 14, wherein said target nucleic acid comprises not less than 50% of the promoter DNA sequence, the ribosome binding sequence, the protein coding sequence, and the terminator or variant terminator DNA sequence.

16. The method of claim 10, wherein the cell-free protein synthesizing system comprises T7 RNA polymerase.

17. The method of claim 10, wherein the cell-free protein synthesizing system comprises an *E. Coli* extract.

* * * * *

SEQUENCE LISTING

<160> NUMBER OF SEQ ID NOS: 13

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 1
gcgagtcagt gagcgaggaa g          21

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 2
cgattcatta atgcagatct cgatccc          27

<210> SEQ ID NO 3
<211> LENGTH: 80
<212> TYPE: DNA
<213> ORGANISM: Artificial Sequence
<220> FEATURE:
<223> OTHER INFORMATION: N is A, T, C, or G
<220> FEATURE:
<223> OTHER INFORMATION: Description of Artificial Sequence:primer

<400> SEQUENCE: 3
aacagtacac gtcgtgccac caaagcagag agctccactg tctcgccaan nngatcaagc          60
ttcgaattct acgaatgcta          80

<210> SEQ ID NO 4

```
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 4
aacagtacac gtcgtgccac c                                         21

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 5
agcagagagc tccactgtct cgcc                                      24

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 6
ccgcgaaatt aatacgactc                                           20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 7
ttattgctca gcggtggcag                                           20

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 8
gccagatccg gatatagttc ctcc                                      24

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 9
agcaaaaaac ccctcaagac c                                         21

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence:primer

<400> SEQUENCE: 10
```

```
agcaaaaatc gtctcaacaa gcgtttagag gccccaaggg gt                    42

<210> SEQ ID NO 11
<211> LENGTH: 41
<212> TYPE: DNA
<213> ORGANISM: Artificial Sequence
<220> FEATURE:
<223> OTHER INFORMATION: Description of Artificial Sequence:primer

<400> SEQUENCE: 11
ggcgagacag tggagctctc tgcccggctg ctaacaaagc c                     41

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 12
ctgcgcaact gttgggaagg g                                           21

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence:T7 Promoter
      sequence

<400> SEQUENCE: 13
taatacgact cactata                                                17
```